(12) United States Patent
Lee et al.

(10) Patent No.: US 12,311,042 B2
(45) Date of Patent: May 27, 2025

(54) INK COMPOSITION FOR HAIR DYEING, FILM FOR HAIR DYEING, FILM CARTRIDGE FOR HAIR DYEING, AND PRINTER FOR HAIR DYEING

(71) Applicant: PRINKER KOREA INC., Suwon-si (KR)

(72) Inventors: Kyu Suk Lee, Suwon-si (KR); Jong In Lee, Suwon-si (KR); Tae Sik Yun, Seoul (KR); Mi Kyoung Han, Anyang-si (KR); Dong Hoon Song, Anyang-si (KR); Yong Min Jeong, Suwon-si (KR)

(73) Assignee: PRINKER KOREA INC., Suwon-si (KR)

( * ) Notice: Subject to any disclaimer, the term of this patent is extended or adjusted under 35 U.S.C. 154(b) by 100 days.

(21) Appl. No.: 18/029,363

(22) PCT Filed: Sep. 27, 2021

(86) PCT No.: PCT/KR2021/013122
§ 371 (c)(1),
(2) Date: Mar. 29, 2023

(87) PCT Pub. No.: WO2022/145632
PCT Pub. Date: Jul. 7, 2022

(65) Prior Publication Data
US 2023/0301880 A1    Sep. 28, 2023

(30) Foreign Application Priority Data
Dec. 31, 2020   (KR) .................. 10-2020-0189854

(51) Int. Cl.
*A61Q 5/10*     (2006.01)
*A61K 8/19*     (2006.01)
*A61K 8/92*     (2006.01)

(52) U.S. Cl.
CPC .............. *A61K 8/19* (2013.01); *A61K 8/92* (2013.01); *A61Q 5/10* (2013.01); *A61K 2800/4324* (2013.01)

(58) Field of Classification Search
CPC .... A61K 8/19; A61K 8/92; A61K 2800/4324; A61K 8/044; A61K 8/26; A61K 8/29;
(Continued)

(56) References Cited

FOREIGN PATENT DOCUMENTS

| JP | 2006503610 A | 2/2006 |
|---|---|---|
| JP | 2015503959 A | 2/2015 |

(Continued)

OTHER PUBLICATIONS

International Search Report and Written Opinion of the International Searching Authority in relation to international application No. PCT/KR2021/013122, dated Apr. 12, 2022, 11 pages.

*Primary Examiner* — Eisa B Elhilo
(74) *Attorney, Agent, or Firm* — Bochner PLLC; Andrew Bochner; Eric Kleinertz

(57) ABSTRACT

According to one aspect of the present disclosure, provided is a film for hair dyeing comprising: a base film; and an ink layer for hair dyeing on the base film, wherein the ink layer for hair dyeing comprises a first pigment for masking hair color, a second pigment for expressing desired color on hair, a resin, and wax. According to one aspect of the present disclosure, provided is a printer for hair dyeing comprising: a body including a printer head; and a film cartridge for hair dyeing mounted to the body over the printer head; wherein the printer head may be in contact with a film included in the film cartridge for hair dyeing and comprises a hair holder of which one end is connected to one end of the body so as to be folded and unfolded with respect to the body. The hair
(Continued)

may be grabbed between the body and the hair holder, and the printer head may be positioned on a side facing the hair holder.

13 Claims, 17 Drawing Sheets

(58) Field of Classification Search
CPC .......... A61K 8/39; A61K 8/922; A61K 8/925; A61K 8/0204; A61K 8/8152; A61K 8/87; A61K 2800/43; A61K 2800/87; A61Q 5/10; A61Q 5/065; A45D 19/00; A45D 19/018; C09D 11/037
USPC ............................................................ 8/405
See application file for complete search history.

(56) References Cited

FOREIGN PATENT DOCUMENTS

| | | | | |
|---|---|---|---|---|
| JP | 2020507558 A | 3/2020 | | |
| KR | 1020010090400 A | 10/2001 | | |
| KR | 20050107814 A | * 11/2005 | ............... | A61Q 1/00 |
| KR | 101985396 B1 | 6/2019 | | |
| WO | 2013093775 A1 | 6/2013 | | |
| WO | 2018104374 A1 | 6/2018 | | |
| WO | WO 2020126773 A1 | * 6/2020 | ............... | A61Q 5/10 |

* cited by examiner

INK COMPOSITION FOR HAIR DYEING, FILM FOR HAIR DYEING, FILM CARTRIDGE FOR HAIR DYEING, AND PRINTER FOR HAIR DYEING

TECHNICAL FIELD

The present disclosure relates to an ink composition for hair dyeing, a film for hair dyeing, and a device for hair dyeing including the same, for use in hair dyeing.

BACKGROUND ART

As a way to make one's hair style, many people choose hair dyeing along with perming and cutting. Types of hair dyeing include permanent dyeing and temporary dyeing. In the case of permanent dyeing, the hair is bleached and dyed, and the dyed color is maintained until new hair grows. In the case of temporary dyeing, a colorant is attached to the hair surface to physically dye the hair.

When hair dyeing is wanted only for a short period of time for a specific event, temporary dyeing is appropriate. However, temporary dyeing has not been popular among consumers due to problems such as dye staining and the like. In addition, the hair dyeing is often done by a beauty expert due to a cumbersome process, and thus is time-consuming and costs a lot.

DISCLOSURE

Technical Problem

The present disclosure provides an ink composition for hair dyeing, a film for hair dyeing, a film cartridge for hair dyeing, and a printer for hair dyeing, for temporary hair dyeing that can be easily done without staining.

Technical Solution

According to an aspect of the present disclosure,
an ink composition for hair dyeing comprises: a first pigment dispersion comprising a first pigment for masking hair color; a second pigment dispersion comprising a second pigment for expressing desired color on hair; a resin; wax; and a solvent.

The first pigment may comprise titanium oxide, tin oxide, zinc oxide, aluminum oxide, silicon dioxide, zirconium oxide, silver(I) oxide, gold, silver, mica, synthetic mica, or a combination thereof.

The second pigment may comprise prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS(CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof.

The resin may include a polymer including at least one unit of acrylate, dimethylsiloxane, cyclopentasiloxane, polyacrylic acid, sodium polyacrylate, partially neutralized polyacrylic acid, polyacrylate starch, carmellose sodium, a carboxyvinyl polymer, an N-vinylacetatamide copolymer, polyurethane, polyester urethane, carboxymethyl cellulose, methyl cellulose, ethyl cellulose, hydroxypropyl cellulose, hydroxypropylmethyl cellulose, hydroxyethyl cellulose, polyvinyl pyrrolidone, polyvinyl alcohol, polyvinyl acetoacetal, polyvinyl butyral, polyquaternium-28, polyquaternium-11, an acrylate/dimethylsilicone copolymer, a vinylacetate/vinylpyrrolidonemonomer copolymer, a vinylpyrrolidone/dimethylamino ethylmetaacrylate copolymer, a styrene/acrylate copolymer, an acrylate/ethylhexylacrylate copolymer, dextrinisostearate, a metacryloyl ethylbetaine/acrylate copolymer, an AMP/acrylate copolymer, cellulose acetate formate, cellulose acetate propionate, and cellulose acetate butylate.

The wax may comprise carnauba wax, lanolin, paraffin, shea butter, beeswax, olive wax, candelilla wax, vegetable wax, cacao butter, microcrystal wax, ceresin wax, cupuacu seed butter, braze, caster oil, polyethylene wax, microcrystalline wax, amide wax, ester wax, oxidation wax, or a combination thereof.

The solvent may comprise distilled water, diethylene glycol butyl ether, ethylene glycol, propylene glycol, polyethylene glycol, glycerin, oleyl alcohol, butylene glycol dimethylsiloxane, cyclopentasiloxane, ethyl alcohol, n-propyl alcohol, isopropyl alcohol, n-butyl alcohol, sec-butyl alcohol, t-butyl alcohol, isobutyl alcohol, ethyl lactate, diethylene glycol, triethylene glycol, dipropylene glycol butylene glycol, 1,4-butanediol, 1,2,4-butanetriol, 1,5-pentanediol, 1,6-hexanediol, 1,2-hexanediol, 1,2,6-hexanetriol, hexylene glycol, glycerol ethoxylate, trimethylolpropane ethoxylate, sodium 2-pyrrolidone-5-carboxylate, methyl pyrrolidone, caprylyl pyrrolidone, erythritol, ethyleneglycol monomethyl ether, ethyleneglycol monoethyl ether, diethylene glycol methyl ether, diethylene glycol ethylether, triethyleneglycol monomethyl ether, triethyleneglycol monoethyl ether, dimethyl sulfoxide, tetramethylene sulfone, thioglycol, methyl carbitol, ethyl carbitol, propyl carbitol, butyl carbitol, alkyl cellosolve, dipropylene glycol alkylether, carbitol monoalkylacetate, propyleneglycol monoalkylether, ethylenecarbonate, propylenecarbonate, butanol, pentanol, hexanol, and 2-ethylhexanol, or a combination thereof. Alkyl among the compounds may be, for example, methyl, ethyl, propyl, butyl, pentyl, hexyl, and the like.

Another aspect of the disclosure, a film for hair dyeing comprises:
a base film; and
an ink layer for hair dyeing on the base film,
wherein the ink layer for hair dyeing comprises: a first pigment for masking hair color; a second pigment for expressing desired color on hair; a resin; and wax.

The base film may include polyethylene terephthalate (PET), polyethylene naphthalate (PEN), polyethylene (PE), polyimide (PI), polycarbonate (PC), polypropylene (PP), polyester, or a combination thereof.

The film for hair dyeing may further include a back film on a side facing the ink layer on the base film.

According to another aspect of the disclosure, a film cartridge for hair dyeing comprises:
a pair of reels comprising a first reel and a second reel;
the aforementioned film for hair dyeing wound around the first reel and having one end connected to the second reel; and
a cartridge housing protecting the first reel, the second reel, and the film and comprising a film-exposing unit positioned between the first reel and the second reel and exposing the film for hair dyeing.

According to another aspect of the disclosure, a printer for hair dyeing comprises:
  a body comprising a printer head; and
  a hair holder of which one end connected to one end of the body so as to be folded and unfolded with respect to the body,
  wherein the hair is grabbed between the body and the hair holder, and
  the printer head may be positioned on a side facing the hair holder.

The film for hair dyeing may be then positioned between the body and the hair.

The printer head may be in contact with the film for hair dyeing.

The printer head may be a thermal transfer type.

The printer for hair dyeing may apply heat to each dot of the printer head independently, so as to form a dyeing pattern on the hair.

The hair holder may be a roller type.

The body may include an operating unit and display unit.

The body may further comprise a cartridge mounting unit to which a film cartridge for hair dyeing can be mounted so as to connect the body with the printer head.

According to another aspect of the disclosure, a method of preparing a film for hair dyeing comprises:
  (a) preparing a mixed dispersion by mixing a first pigment dispersion including a first pigment for masking hair color and a second pigment dispersion including a second pigment for expressing desired color on hair;
  (b) preparing an ink composition for hair dyeing by adding and mixing a resin, wax, and a third solvent to the mixed dispersion;
  (c) coating the ink composition for hair dyeing on a base film; and
  (d) drying the base film coated with the ink composition for hair dyeing.

In step (a), the first pigment dispersion and the second pigment dispersion may be prepared by dispersion using bead mills.

The first pigment dispersion may further comprise a first dispersant and a first solvent, and
  the second pigment dispersion may further comprise a second dispersant and a second solvent.

The first pigment may comprise titanium oxide, tin oxide, zinc oxide, aluminum oxide, silicon dioxide, zirconium oxide, silver(I) oxide, gold, silver, mica, synthetic mica, or a combination thereof.

The second pigment may comprise prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS(CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof.

The resin may include a polymer including at least one unit of acrylate, dimethylsiloxane, cyclopentasiloxane, polyacrylic acid, sodium polyacrylate, partially neutralized polyacrylic acid, polyacrylate starch, carmellose sodium, a carboxyvinyl polymer, an N-vinylacetatamide copolymer, polyurethane, polyester urethane, carboxymethyl cellulose, methyl cellulose, ethyl cellulose, hydroxypropyl cellulose, hydroxypropylmethyl cellulose, hydroxyethyl cellulose, polyvinyl pyrrolidone, polyvinyl alcohol, polyvinyl acetoacetal, polyvinyl butyral, polyquaternium-28, polyquaternium-11, an acrylate/dimethylsilicone copolymer, a vinylacetate/vinylpyrrolidonemonomer copolymer, a vinylpyrrolidone/dimethylamino ethylmetaacrylate copolymer, a styrene/acrylate copolymer, an acrylate/ethylhexylacrylate copolymer, dextrinisostearate, a metacryloyl ethylbetaine/acrylate copolymer, an AMP/acrylate copolymer, cellulose acetate formate, cellulose acetate propionate, and cellulose acetate butylate.

The wax may comprise carnauba wax, lanolin, paraffin, shea butter, beeswax, olive wax, candelilla wax, vegetable wax, cacao butter, microcrystal wax, ceresin wax, cupuacu seed butter, braze, caster oil, polyethylene wax, microcrystalline wax, amide wax, ester wax, oxidation wax, or a combination thereof.

Advantageous Effects

By using a composition for hair dyeing, a film for hair dyeing, a film cartridge for hair dyeing, and a printer for hair dyeing according to embodiments of the present disclosure, the hair can be temporarily dyed in a quick and easy way. In addition, the dye of the hair dyed according to embodiments can be easily removed by shampoo or the like.

BEST MODE

Figure 1:
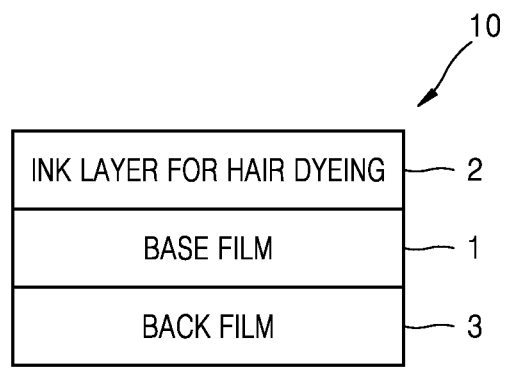
FIG. 1 is a conceptual cross-sectional view of a film for hair dyeing according to an embodiment.

In the present specification, the term 'hair dyeing' is used for kinds of color implementation on hair, such as hair dyeing by coloring as well as hair dyeing by redox process.

In the present specification, the term 'film for hair dyeing' refers to a film used for dyeing hair by transferring ink for hair dyeing from a film to the hair.

In the present specification, the term 'dyeing pattern' refers that only a part of the hair is dyed and the dyed portion has a pattern such as a bar shape, a star shape, or a letter shape.

Hereinafter, a composition for hair dyeing according to an embodiment of the present disclosure will be described in detail.

(Ink Composition for Hair Dyeing)

An ink composition for hair dyeing according to an embodiment may include: a first pigment for masking hair color; a second pigment for expressing desired color on hair; a resin; a dispersant; wax; and a solvent.

The first pigment is a pigment used first for masking the original hair color to dye the hair desired color. The first pigment may specifically include titanium oxide, tin oxide, zinc oxide, aluminum oxide, silicon dioxide, zirconium oxide, silver(I) oxide, gold, silver, mica, synthetic mica, or a combination thereof, but embodiments are not limited thereto. For example, a titanium oxide pigment may be attached to the hair to express white color by masking the original color of the hair. The content of the first pigment may be about 1 wt % to about 40 wt % based on the entire ink composition for hair dyeing.

The second pigment may be a pigment for presenting desired color on the hair whose original color is masked by the first pigment. As the second pigment, various pigments may be used according to desired color. The second pigment may include, for example, prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS(CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof, but embodiments are not limited thereto. The first pigment and the second pigment may include, for example, particles having a diameter of 150 nm to 1,000 nm. The content of the second pigment may be about 1 wt % to about 40 wt % based on the entire ink composition for hair dyeing.

The resin may provide transfer characteristics by imparting adhesion strength to a base film and hair when forming a film for hair dyeing in which the first pigment and the second pigment are dispersed. The resin may include, for example, a polymer including at least one unit of acrylate, dimethylsiloxane, cyclopentasiloxane, polyacrylic acid, sodium polyacrylate, partially neutralized polyacrylic acid, polyacrylate starch, carmellose sodium, a carboxyvinyl polymer, an N-vinylacetatamide copolymer, polyurethane, polyester urethane, carboxymethyl cellulose, methyl cellulose, ethyl cellulose, hydroxypropyl cellulose, hydroxypropylmethyl cellulose, hydroxyethyl cellulose, polyvinyl pyrrolidone, polyvinyl alcohol, polyvinyl acetoacetal, polyvinyl butyral, polyquaternium-28, polyquaternium-11, an acrylate/dimethylsilicone copolymer, a vinylacetate/vinylpyrrolidonemonomer copolymer, a vinylpyrrolidone/dimethylamino ethylmetaacrylate copolymer, a styrene/acrylate copolymer, an acrylate/ethylhexylacrylate copolymer, dextrinisostearate, a metacryloyl ethylbetaine/acrylate copolymer, an AMP/acrylate copolymer, cellulose acetate formate, cellulose acetate propionate, and cellulose acetate butylate. The resin may be, for example, an acrylate/dimethylsilicone copolymer. The content of the resin may be about 1 wt % to about 30 wt % based on the entire ink composition for hair dyeing.

The dispersant is a component for assisting dispersion of first pigment and the second pigment, and may use polyvinyl pyrrolidone, polyvinyl alcohol, polyvinyl acetate, a pyrrolidone/acrylic acid copolymer, a pyrrolidone/methacrylic acid copolymer, a styrene/acrylic acid copolymer, a styrene/methacrylic acid copolymer, a styrene/maleic anhydride copolymer, an acrylic acid alkyl ester/acrylic acid copolymer, a methacrylic acid alkyl ester/acrylic acid copolymer, polyvinyl oxazoline, polyvinyl imidazole, polyethylene glycol, polypropylene glycol, a polyglyceryl-ester-based dispersant, such as polyquaternium-51, polyquaternium-10, glyceryl stearate, polysorbate 20, polysorbate 80, polysorbate 60, lecithin, polyglyceryl-10 laurate, and polyglyceryl-6 polyricinoleate, a polyglycerin fatty acid ester-based dispersant, or a combination thereof. Alkyl among the compounds may be, for example, methyl, ethyl, propyl, butyl, pentyl, hexyl, and the like.

In addition, for use as the dispersant, a commercially available dispersant may be used. For example, DISPERBYK-111, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-2155, DISPERBYK-180, DISPERBYK-194 N, TEGO® Dispers 755 W, Efka® PX 4300, Efka® PX 4320, Efka PX 4340, TEGO® Dispers 655, or a combination thereof may be used as the dispersant, but embodiments are not limited thereto. The content of the dispersant may be about 1 wt % to about 30 wt % based on the entire ink composition for hair dyeing.

The wax may further impart adhesion strength to the ink for hair dyeing on the hair, and may facilitate the ink to transfer from a base, such as a film, to the hair when heat is applied. The wax may use, for example, carnauba wax, lanolin, paraffin, shea butter, beeswax, olive wax, candelilla wax, vegetable wax, cacao butter, microcrystal wax, ceresin wax, cupuacu seed butter, braze, caster oil, polyethylene wax, microcrystalline wax, amide wax, ester wax, oxidized wax, or a combination thereof, but embodiments are not limited thereto. The content of the wax may be about 1 wt % to about 30 wt % based on the entire ink composition for hair dyeing.

The solvent may use distilled water, diethylene glycol butyl ether, ethylene glycol, propylene glycol, polyethylene glycol, glycerin, oleyl alcohol, butylene glycol dimethylsiloxane, cyclopentasiloxane, ethyl alcohol, n-propyl alcohol, isopropyl alcohol, n-butyl alcohol, sec-butyl alcohol, t-butyl alcohol, isobutyl alcohol, ethyl lactate, diethylene glycol, triethyleneglycol, dipropyleneglycol butylene glycol, 1,4-butanediol, 1,2,4-butanetriol, 1,5-pentanediol, 1,6-hexanediol, 1,2-hexanediol, 1,2,6-hexanetriol, hexylene glycol, glycerol ethoxylate, trimethylolpropane ethoxylate, sodium 2-pyrrolidone-5-carboxylate, methyl pyrrolidone, caprylyl pyrrolidone, erythritol, ethyleneglycol monomethyl ether, ethyleneglycol monoethyl ether, diethylene glycol methyl ether, diethylene glycol ethylether, triethyleneglycol monomethyl ether, triethyleneglycol monoethyl ether, dimethyl sulfoxide, tetramethylene sulfone, thioglycol, methyl carbitol, ethyl carbitol, propyl carbitol, butyl carbitol, alkyl cellosolve, dipropylene glycol alkylether, carbitol monoalkylacetate, propyleneglycol monoalkylether, ethylenecarbonate, propylenecarbonate, butanol, pentanol, hexanol, 2-ethelhexanol, or a combination thereof, but embodiments are not limited thereto. Alkyl among the compounds may be, for example, methyl, ethyl, propyl, butyl, pentyl, hexyl, and the like.

The composition for hair dyeing may be used to prepare a film for hair dyeing for temporary hair dyeing.

Hereinafter, a film for hair dyeing according to an embodiment of the present disclosure will be described in detail.

(Film for Hair Dyeing)

FIG. 1 is a conceptual cross-sectional view of a film for hair dyeing 10 according to an embodiment. Referring to FIG. 1, the film for hair dyeing 10 includes a base film 1 and an ink layer for hair dyeing 2 on the base film. The ink layer for hair dyeing 2 may include a first pigment for masking current color of the hair, a second pigment for expressing desired color on the hair, a resin, and wax.

For use as the base film 1, a heat-resistant film for supporting and transferring the ink layer for hair dyeing 2 may be used. For use as the base film 1, a polyethylene terephthalate (PET), film for hair dyeing may be provided.

The base film 1 may use PET, polyethylene naphthalate (PEN), polyethylene (PE), polyimide (PI), polycarbonate (PC), polypropylene (PP), polyester, or a combination thereof, but embodiments are not limited thereto. The base film 1 may have, for example, a thickness in a range of 2 micron (μm) to 20 μm.

The ink layer for hair dyeing 2 is a layer in which an ink for hair dyeing is transferred to the hair to dye the hair. The ink layer for hair dyeing 2 may comprise a first pigment and a second pigment that are capable of coloring the hair. The first pigment is a pigment used first for masking the original hair color to dye the hair desired color. The first pigment may specifically include titanium oxide, tin oxide, zinc oxide, aluminum oxide, silicon dioxide, zirconium oxide, silver(I) oxide, gold, silver, mica, synthetic mica, or a combination thereof, but embodiments are not limited thereto. For example, a titanium oxide pigment may be attached to the hair to express white color by masking the original color of the hair.

The second pigment may be a pigment for presenting desired color on the hair whose original color is masked by the first pigment. As the second pigment, various pigments may be used according to desired color. The second pigment may include, for example, prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS(CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof, but embodiments are not limited thereto. The first pigment and the second pigment may be, for example, particles having a diameter of 150 nm to 1,000 nm.

The ink layer for hair dyeing 2 may further include a resin and wax.

The resin may provide transfer characteristics by dispersing the first pigment and the second pigment in the ink layer for hair dyeing 2 and imparting adhesion strength to the ink layer for hair dyeing 2 on the base film 1 and the hair. The resin may consist of, for example, a polymer including at least one unit of acrylate, dimethylsiloxane, cyclopentasiloxane, polyacrylic acid, sodium polyacrylate, partially neutralized polyacrylic acid, polyacrylate starch, carmellose sodium, a carboxyvinyl polymer, an N-vinylacetatamide copolymer, polyurethane, polyester urethane, carboxymethyl cellulose, methyl cellulose, ethyl cellulose, hydroxypropyl cellulose, hydroxypropylmethyl cellulose, hydroxyethyl cellulose, polyvinyl pyrrolidone, polyvinyl alcohol, polyvinyl acetoacetal, polyvinyl butyral, polyquaternium-28, polyquaternium-11, an acrylate/dimethylsilicone copolymer, a vinylacetate/vinylpyrrolidonemonomer copolymer, a vinylpyrrolidone/dimethylamino ethylmetaacrylate copolymer, a styrene/acrylate copolymer, an acrylate/ethylhexylacrylate copolymer, dextrinisostearate, a metacryloyl ethylbetaine/acrylate copolymer, an AMP/acrylate copolymer, cellulose acetate formate, cellulose acetate propionate, and cellulose acetate butylate. The resin may be, for example, a copolymer of acrylate and dimethylsilicone.

The wax may further impart adhesion strength to the ink layer for hair dyeing 2 on the hair, and may facilitate transfer from a base, such as a film, to the hair when heat is applied. The wax may use, for example, carnauba wax, lanolin, paraffin, shea butter, beeswax, olive wax, candelilla wax, vegetable wax, cacao butter, microcrystal wax, ceresin wax, cupuacu seed butter, braze, caster oil, polyethylene wax, microcrystalline wax, amide wax, ester wax, oxidation wax, or a combination thereof, but embodiments are not limited thereto.

Meanwhile, when the ink layer for hair dyeing 2 is formed from the composition for hair dyeing, a portion of a solvent from the composition for hair dyeing may remain in the ink layer for hair dyeing 2.

The ink layer for hair dyeing 2 may, for example, have a thickness in a range of 1 μm to 100 μm.

In an embodiment, the film for hair dyeing 10 may further include a back film 3 on the base film 1 opposite to the ink layer for hair dyeing 2. The back film 3 may have heat resistance and lubricity. The back film 3 may include, for example, a component such as a silicone-acrylic polymer, a polyimide siloxane copolymer, polyimide, a silicone resin, a mixture of a cellulose-based binder a modified silicone-based polymer, silicone oil, a fatty acid metal salt, phosphate ester, metal stearyl phosphate, an acryl polymer, a polyvinylacetal resin, a polyester resin, amino acid modified silicone oil, etc. The back film 3 may have, for example, a thickness in a range of 0.5 μm to 2 μm.

The film for hair dyeing 10 according to the aforementioned embodiment may be applied directly to the hair or adopted in a film cartridge for hair dyeing for use in hair dyeing.

Hereinafter, a film cartridge for hair dyeing according to an embodiment of the present disclosure will be described in detail.

(Film Cartridge for Hair Dyeing)

Figure 2A:
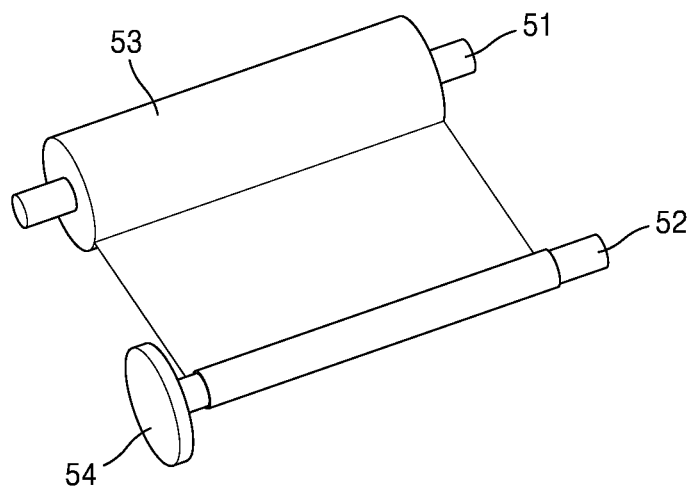
FIGS. 2A and 2B are each schematic perspective views of an inner film included in a film cartridge for hair dyeing and an external cartridge housing of the film cartridge for hair dyeing.
Figure 2B:
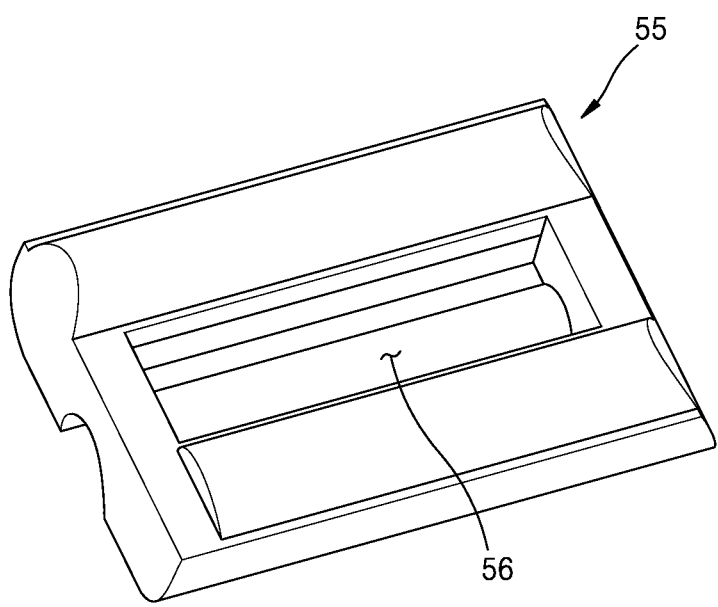
Figure 2C:
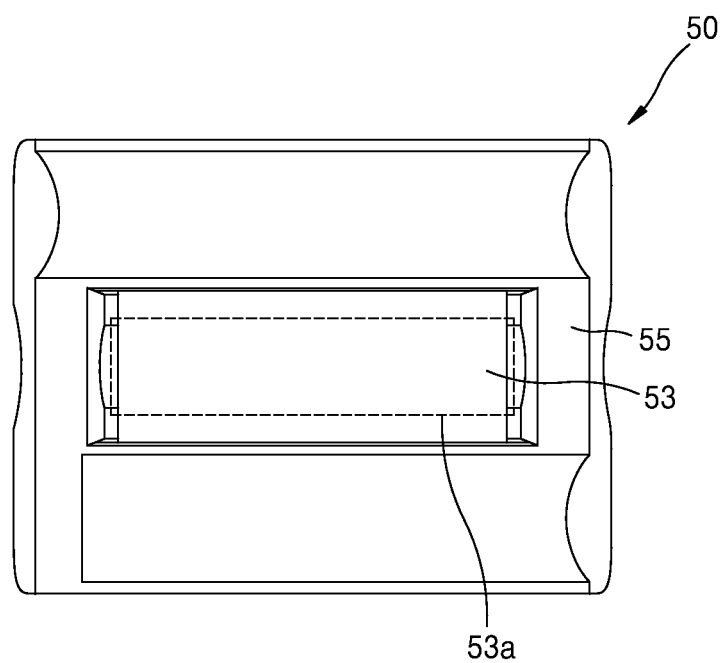
FIG. 2C is a top view of a film cartridge for hair dyeing to which a film is mounted, according to an embodiment.

FIGS. 2A and 2B are each schematic perspective views of an inner film included in a film cartridge for hair dyeing 50 (FIG. 2A) and an external cartridge housing of the film cartridge for hair dyeing 50 (FIG. 2B). FIG. 2C is a top view of the film cartridge for hair dyeing 50 to which a film is mounted, according to an embodiment. The film cartridge for hair dyeing 50 may enable to directly supply a film for hair dyeing to the hair from a printer for hair dyeing without the need to separately spread a film for hair dyeing on the hair.

Referring to FIGS. 2A to 2C, the film cartridge for hair dyeing 50 may include, inside the cartridge housing 55, a first reel 51, a second reel 52, and a film 53 for hair dyeing wound around the first reel 51 and the second reel 52. For use as the film 53 for hair dyeing, the aforementioned film for hair dyeing 10 may be used. Before using the film cartridge 50, the film 53 is wound around the first reel 51, and one end of the film 53 is connected to the second reel 52. The second reel 52 is connected to a driving gear 54. When the film cartridge 50 is inserted into a printer for hair dyeing and used, a wound portion of the film 53 around the first reel 1 is moved to and wound around the second reel 52 by rotation of the second reel 52 so that the film 53 is exposed through a film-exposing unit 56 of the film cartridge 50. In FIG. 2C, among the film 53 exposed through the film-exposing unit 56, a portion 53a of the film 53 to be contacted by a printer head is indicated by a dotted line. The ink layer 2 of the film 53 heated by contact with a printer head of a printer for hair dyeing is transferred to the hair, enabling hair dyeing.

Hereinafter, a printer for hair dyeing according to an embodiment of the present disclosure will be described in detail.

(Printer for Hair Dyeing)

Figure 3A:
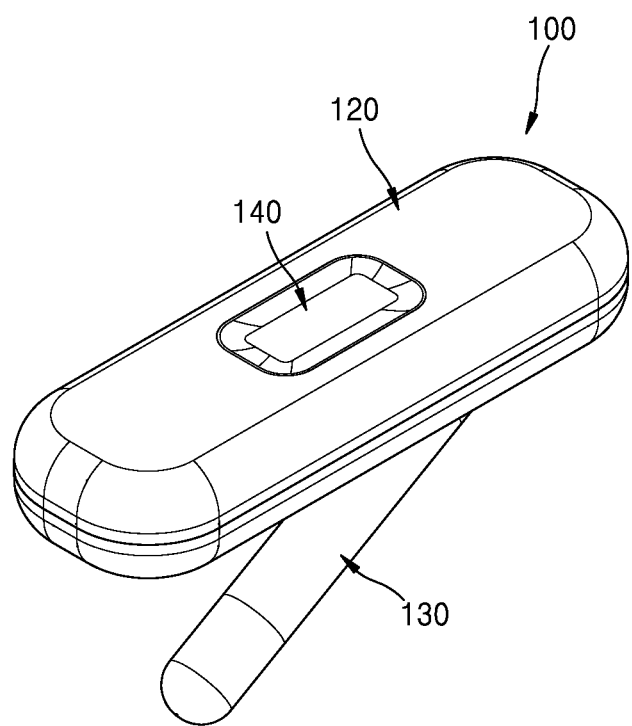
FIGS. 3A and 3B are schematic perspective views of a printer for dyeing hair according to an embodiment.
Figure 3B:
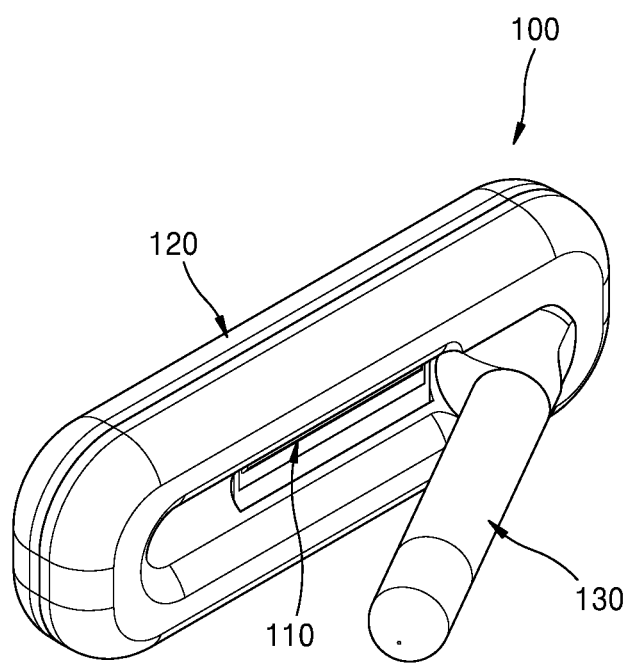

FIGS. 3A and 3B are schematic perspective views of a printer for hair dyeing 100 according to an embodiment. Referring to FIGS. 3A and 3B, the printer for hair dyeing 100 includes: a body 120 including a printer head 110; and a hair holder 130 of which one end is connected to one end of the body 120 so as to be folded and unfolded with respect to the body 120. The body 120 and the hair holder 130 may be connected together by, for example, a hinge method.

The printer head 110 may be a thermal transfer type, and is positioned on a surface facing the hair holder 130. In an embodiment, the body 120 may include an operating unit and display unit 140 (referred with one reference number) on a counter side of the printer head 110. In another embodiment, the operating unit and display unit 140 may be positioned on the lateral side of the body 120. The operating unit and display unit 140 controls the operation of the printer for hair dyeing 100 and displays information related to the operation. The operating unit and display unit 140 may include, for example, a power, a temperature controller, a dyeing pattern controller, or the like of the printer for hair dyeing 100. The hair holder 130 may be a roller type to easily move over the hair. Alternatively, the hair holder 130 may be a plate type to easily move over the hair.

When the hair is grabbed between the body 120 and the hair holder 130 and pressed down with the film for hair dyeing covering the hair, the hair and the film for hair dyeing may be brought into close contact. Here, the ink layer for hair dyeing is transferred from the film for hair dyeing, which is heated by the printer head 110, to the hair so that the hair can be printed. Thus, while holding the printer for hair dyeing by hand and moving it over the hair, the hair may be partially or entirely dyed by printing. In addition, patterns may be printed on the hair.

Figure 4A:
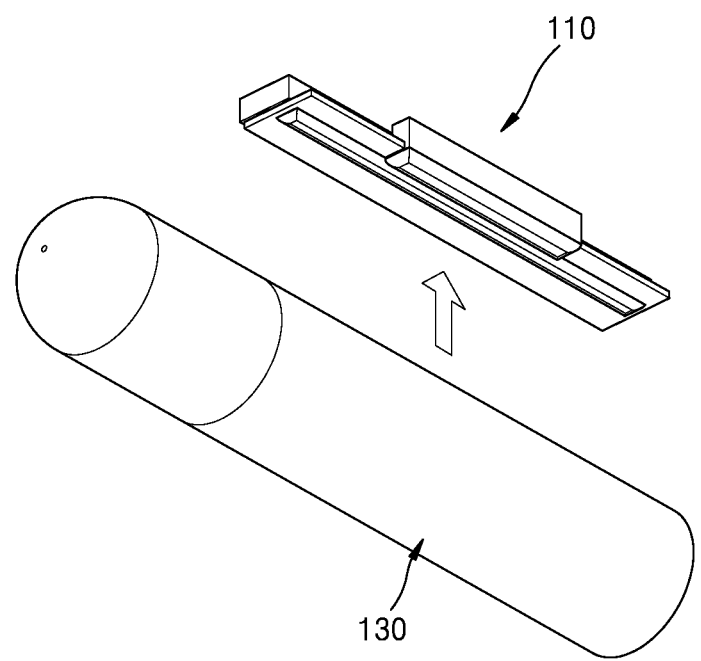
FIG. 4A is an exploded perspective view schematically illustrating positions of a printer head and a hair holder.
Figure 4B:
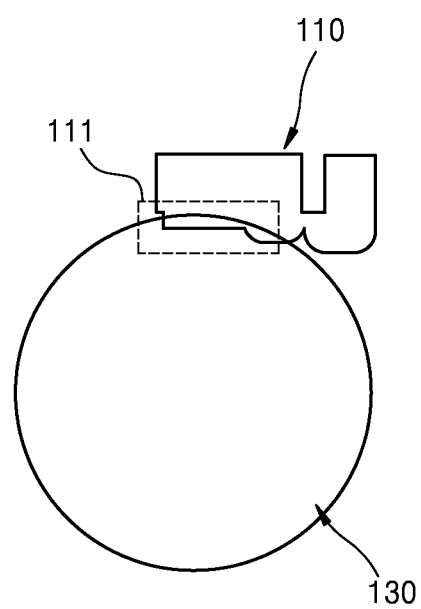
FIG. 4B is a conceptual view of a printer head that is in close contact with a hair holder during operation of a printer for hair dyeing.
Figure 4C:
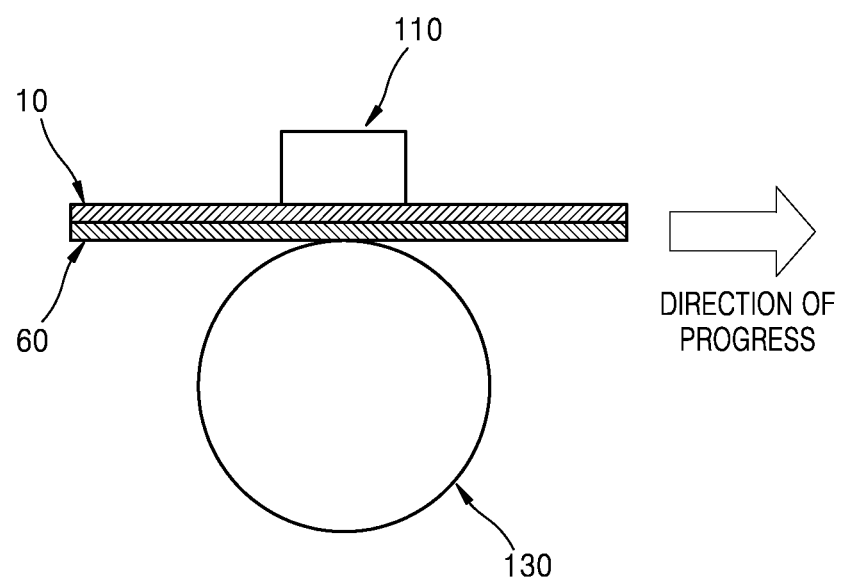
FIG. 4C is a conceptual cross-sectional view schematically illustrating positions of a printer head, a hair holder, a film, and hair when a printer for hair dyeing is in use.

FIG. 4A is an exploded perspective view schematically illustrating positions of the printer head 110 and the hair holder 130, and FIG. 4B is a conceptual view of the printer head 110 that is in close contact with the hair holder 130 during operation of the printer for hair dyeing 100. FIG. 4C is a conceptual cross-sectional view schematically illustrating positions of the printer head 110, the hair holder 130, the film 10, and the hair when the printer for hair dyeing 100 is in use.

Referring to FIG. 4A, the printer head 110 and the hair holder 130 face each other, and come into close contact with each other during hair printing. Referring to FIG. 4B, when the printer head 110 and the hair holder 130 are in close contact with each other, a heating unit 111 of the printer head 110 is in close contact with the hair holder 130. Referring to FIG. 4C, when the body 120 and the hair holder 130 of the printer for hair dyeing 100 are interlocked, the printer head 110 of the body 120 and the film for hair dyeing 10 on the hair 60 are in contact. Accordingly, an ink layer for hair dyeing of the film for hair dyeing 10 may contact the hair 60. When the printer for hair dyeing 100 operates, heat is transferred from the printer head 110 to the film for hair dyeing 10, and an ink layer for hair dyeing of the heated portion of the film for hair dyeing 10 is then transferred from the film for hair dyeing 10 to the hair 60 to dye the hair 60.

The printer head 110 may include a plurality of heating elements (not shown) for heat transfer. The plurality of heating elements (not shown) independently generate heat in various patterns according to a signal from the operating unit of the printer for hair dyeing 100, and thus the hair 60 can be partially dyed to have a dyeing pattern. Alternatively, when the plurality of heating elements (not shown) entirely generate heat, the hair 60 can be dyed as a whole without forming a dyeing pattern. That is, an entire area or a pattern of an ink layer for hair dyeing (not shown) which is in contact with the printer head 110 may be transferred to the hair 60 according to the heating pattern of the printer head 110 so that the hair 60 may be dyed entirely or in a pattern. The printer head 110 may be heated at a temperature in a range of about 50° C. to about 300° C.

Hereinafter, the printer for hair dyeing according to another embodiment of the present disclosure will be described in detail.

Figure 5A:
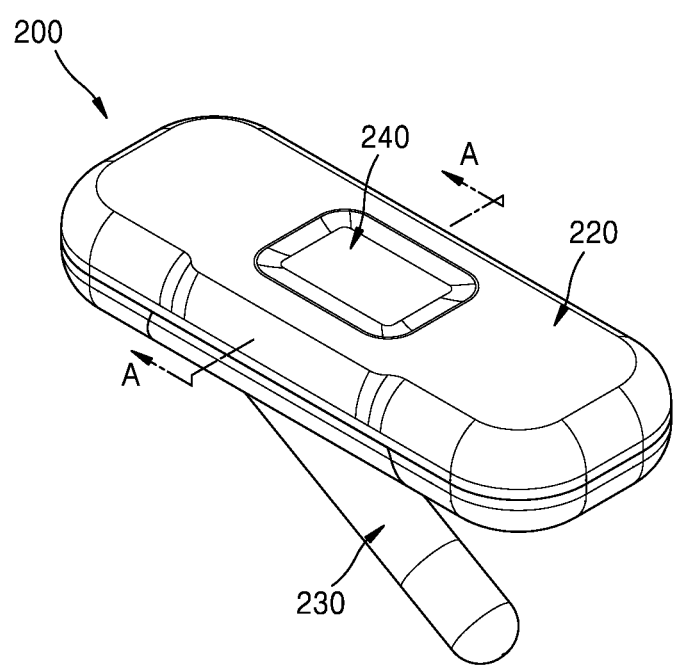
FIGS. 5A and 5B are each schematic perspective views of a printer for hair dyeing including a film cartridge for hair dyeing according to an embodiment.
Figure 5B:
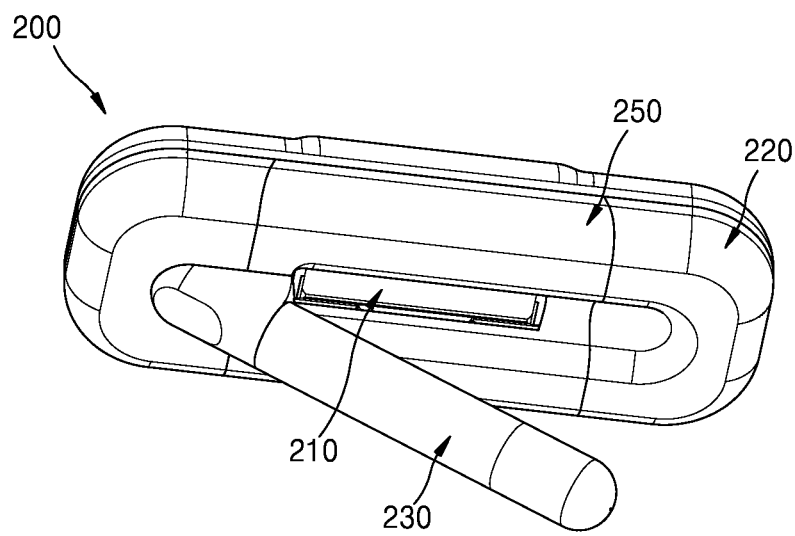

FIGS. 5A and 5B are each schematic perspective views of a printer for hair dyeing 200 including a film cartridge for hair dyeing according to an embodiment.

Referring to FIGS. 5A and 5B, the printer for hair dyeing 200 includes, as in the aforementioned printer for hair dyeing 100, a body 220 including a printer head 210 and a hair holder 230 having one end connected to one end of the body 220 so as to be folded and unfolded with respect to the body 220. The body 220 and the hair holder 230 may be connected together by, for example, a hinge method. The printer head 210 may be a thermal transfer type, and is positioned on a surface facing the hair holder 230. The printer head 210 may be heated at a temperature in a range of about 50° C. to about 300° C. In an embodiment, the body 220 may include an operating unit and display unit 240 on a counter surface of the printer head 210. In another embodiment, the operating unit and display unit 240 may be positioned on the lateral side of the body 220. The operating unit and display unit 240 controls the operation of the printer for hair dyeing 200 and displays information related to the operation. The operating unit and display unit 240 may include, for example, a power, a temperature controller, a dyeing pattern controller, or the like of the printer for hair dyeing 200. The hair holder 230 may be a roller type to easily move over the hair. Alternatively, the hair holder 230 may be a plate type to easily move over the hair.

Unlike the aforementioned printer for hair dyeing 100, the printer for hair dyeing 200 may mount a film cartridge for hair dyeing 250 to the body 220. For use as the film cartridge for hair dyeing 250, the aforementioned film cartridge for hair dyeing 50 may be used. A film-exposing unit (not shown) of the film cartridge for hair dyeing 250 overlaps the printer head 210 of the body 220.

Figure 6A:
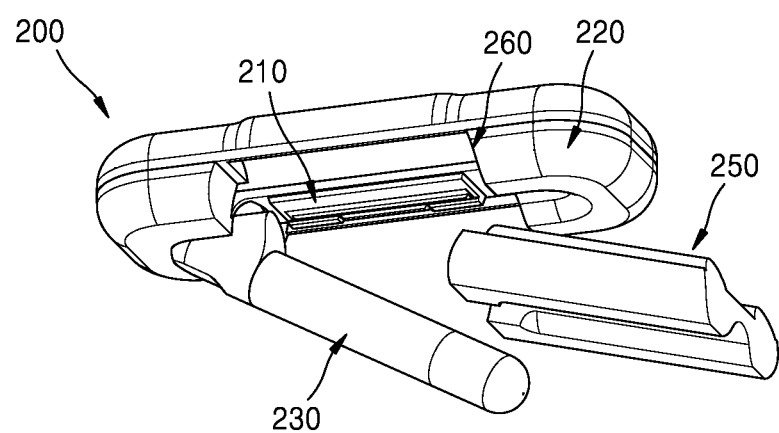
FIGS. 6A to 6C are diagrams illustrating a process of mounting a film cartridge for hair dyeing to a printer for hair dyeing.
Figure 6B:
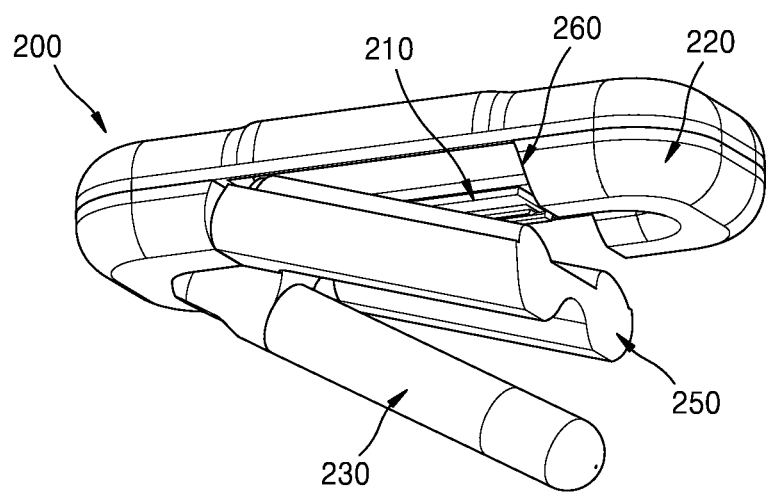
Figure 6C:
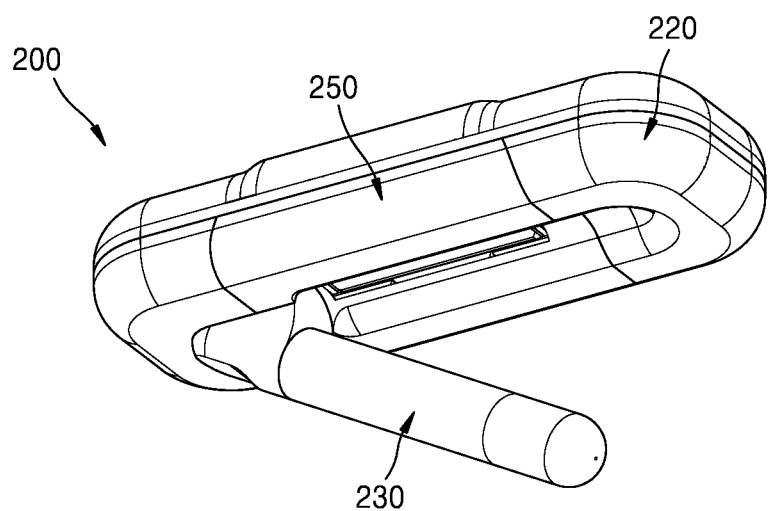

FIGS. 6A to 6C are diagrams illustrating a process of mounting the film cartridge for hair dyeing 250 to the printer for hair dyeing 200. In FIG. 6A, a cartridge mounting unit 260 is located on a lower surface of the body 220. The printer head 210 is exposed to the cartridge mounting unit 260. FIG. 6B illustrates a process in which one end of the film cartridge for hair dyeing 250 is inserted into the cartridge mounting unit 260. FIG. 6C illustrates a state in which the film cartridge for hair dyeing 250 is completely inserted into the cartridge mounting unit 260.

In this regard, since the printer for hair dyeing 200 includes the film cartridge for hair dyeing 250, and thus there is no need to separately apply a film for hair dyeing to the hair so that the hair can be dyed more conveniently. That is, when the hair is grabbed between the body 220 and the hair holder 230 and pressed down, the film for hair dyeing included in the film cartridge 250 may closely contact the hair. Here, an ink layer for hair dyeing is transferred from the film for hair dyeing, which is heated by the printer head 210, to the hair so that the hair can be printed. Thus, while holding the printer for hair dyeing by hand and moving it over the hair, the hair may be partially or entirely died by printing. In addition, patterns may be printed on the hair.

Figure 7:
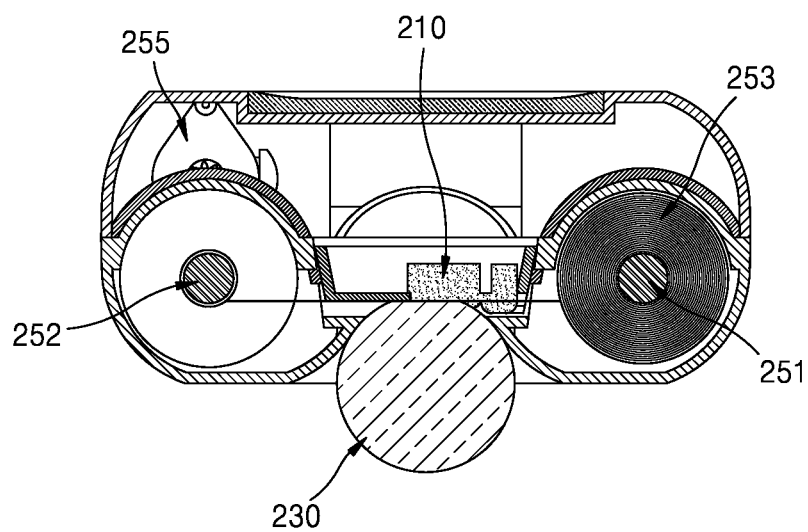
FIG. 7 is a cross-sectional view of a printer for hair dyeing cut along the line A-A' in FIG. 5A.
Figure 8:
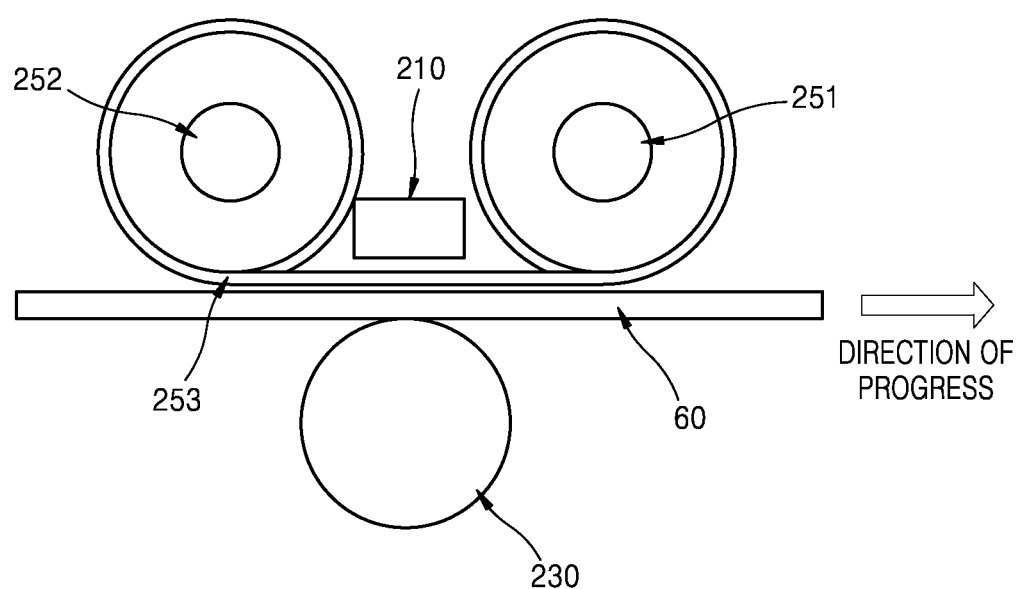
FIG. 8 is a conceptual cross-sectional view illustrating positions of a printer head, a film cartridge for hair dyeing, a hair holder, and hair when a printer for hair dyeing is used.

FIG. 7 is a cross-sectional view of the printer for hair dyeing 200 cut along the line A-A' in FIG. 5A, and FIG. 8 is a conceptual cross-sectional view illustrating positions of the printer head 210, the film cartridge for hair dyeing 250, the hair holder 230, and the hair 60 when using the printer for hair dyeing 200.

Referring to FIGS. 7 and 8, when using the printer for hair dyeing 200, the hair 60 is grabbed between the body 220 and the hair holder 230, and the film for hair dyeing 253 which is spread between two reels 251 and 252 of the film cartridge for hair dyeing 250 contacts the printer head 210 upwardly and contacts the hair 60 on the hair holder 230. The reference number 255 in the drawing indicates a motor driving the reels 251 and 252. The hair holder 230 applies pressure so that the hair 60 contacts the exposed portion of the film for hair dyeing 253 of the printer for hair dyeing 200. When operating the printer for hair dyeing 200, heat is transferred from the printer head 210 to the film for hair dyeing 253 included in the cartridge 250, and an ink layer for dyeing (not shown) of a portion to which the heat is transferred is then transferred from the film for hair dyeing 253 to the hair 60.

As in the printer for hair dyeing 100, the printer head 210 includes a plurality of heating elements (not shown) for thermal transfer. The plurality of heating elements (not shown) independently generate heat in various patterns according to a signal from the operating unit of the printer for hair dyeing 200, and thus the hair 60 can be partially dyed to have a dyeing pattern. Alternatively, when the plurality of heating elements (not shown) entirely generate heat, the hair 60 can be dyed as a whole without forming a dyeing pattern. That is, an entire area or a pattern of an ink layer for hair dyeing (not shown) which is in contact with the printer head 210 may be transferred to the hair 60 according to the heating pattern of the printer head 210 so that the hair 60 may be dyed entirely or in a pattern.

(Preparation Method of Film for Hair Dyeing)

Hereinafter, a method of preparing a film for hair dyeing according to an embodiment of the present disclosure will be described in detail.

To prepare a film for hair dyeing, an ink composition for hair dyeing is prepared first, and then applied to a base film to form an ink layer for hair dyeing.

Figure 9:
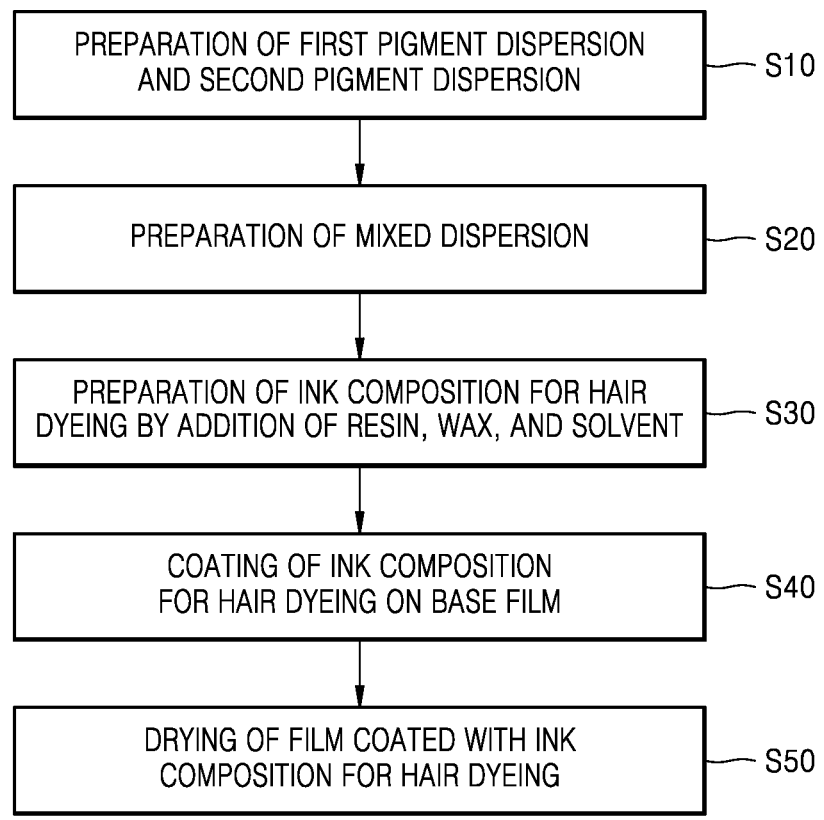
FIG. 9 is a flowchart for sequentially explaining a method of preparing a film for hair dyeing.

FIG. 9 is a flowchart for sequentially explaining a method of preparing a film for hair dyeing.

Referring to FIG. 9, first, a first pigment dispersion and a second pigment dispersion may be prepared (S10). The first pigment dispersion refers to a dispersion containing a first pigment, a first dispersant, and a first solvent, and the second pigment dispersion refers to a dispersion containing a second pigment, a second dispersant, and a second solvent.

The first pigment is a pigment used first for masking the original or current hair color to dye the hair desired color. The first pigment may include, for example, titanium oxide, tin oxide, zinc oxide, aluminum oxide, silicon dioxide, zirconium oxide, silver(I) oxide, gold, silver, mica, synthetic mica, or a combination thereof, but embodiments are not limited thereto. The first pigment may be a pigment that dyes the hair color lightly so that another color can be dyed thereon. For example, titanium oxide can be colored on the hair to mask the original color of the hair and present white color, and thus can be used as the first pigment. The content of the first pigment may be about 10 wt % to about 60 wt % based on the entire first pigment dispersion.

The first dispersant may use, as a material added to the first solvent to prevent aggregation of the first pigment, a surfactant or a polymer. For use as the first dispersant, polyvinylpyrrolidone, polyvinyl alcohol, polyvinyl acetate, a pyrrolidone/acrylic acid copolymer, a pyrrolidone/methacrylic acid copolymer, a styrene/acrylic acid copolymer, a styrene/methacrylic acid copolymer, a styrene/maleic anhydride copolymer, an acrylic acid alkyl ester/acrylic acid copolymer, a methacrylic acid alkyl ester/acrylic acid copolymer, polyvinyl oxazoline, polyvinyl imidazole, polyethylene glycol, polypropylene glycol, a polyglyceryl-ester-based dispersant, such as polyquaternium-51, polyquaternium-10, glyceryl stearate, polysorbate 20, polysorbate 80, polysorbate 60, lecithin, polyglyceryl-10 laurate, and polyglyceryl-6 polyricinoleate, a polyglycerin fatty acid ester-based dispersant, or a combination thereof. Alkyl among the compounds may be, for example, methyl, ethyl, propyl, butyl, pentyl, hexyl, and the like.

In addition, for use as the dispersant, a commercially available dispersant may be used. For example, the dispersant may include DISPERBYK-111, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-2155, DISPERBYK-180, DISPERBYK-194 N, TEGO® Dispers 755 W, Efka® PX 4300, Efka® PX 4320, Efka PX 4340, TEGO® Dispers 655, or a combination thereof, but embodiments are not limited thereto.

The content of the first dispersant may be about 1 wt % to about 30 wt % based on the entire first pigment dispersion. When the contents of the first pigment and the first dispersant are within the ranges above, the first pigment dispersion may have excellent dispersibility leading to long-term stability, and have uniform hair-masking characteristics.

The first solvent may use, as a solvent for forming the first pigment dispersion, distilled water, diethylene glycol butyl ether, ethylene glycol, propylene glycol, polyethylene glycol, glycerin, oleyl alcohol, butylene glycol dimethylsiloxane, cyclopentasiloxane, ethyl alcohol, n-propyl alcohol, isopropyl alcohol, n-butyl alcohol, sec-butyl alcohol, t-butyl alcohol, isobutyl alcohol, ethyl lactate, diethylene glycol, triethylene glycol, dipropylene glycol, butylene glycol, 1,4-butanediol, 1,2,4-butanetriol, 1,5-pentanediol, 1,6-hexanediol, 1,2-hexanediol, 1,2,6-hexanetriol, hexylene glycol, glycerol ethoxylate, trimethylol propane ethoxylate, sodium 2-pyrrolidone-5-carboxylate, methyl pyrrolidone, caprylyl pyrrolidone, erythritol, ethyleneglycol monomethyl ether, ethyleneglycol monoethyl ether, diethylene glycol methyl ether, diethylene glycol ethyl ether, triethyleneglycol monomethyl ether, triethyleneglycol monoethyl ether, dimethyl sulfoxide, tetramethylene sulfone, thioglycol, methylcarbitol, ethylcarbitol, propylcarbitol, butylcarbitol, alkyl cellosolve, dipropylene glycol alkyl ether, carbitol monoalkyl acetate, propylene glycol monoalkyl ether, ethylene carbonate, propylene carbonate, butanol, pentanol, hexanol, 2-ethylhexanol, or a combination thereof, but embodiments are not limited thereto. Alkyl among the compounds may be, for example, methyl, ethyl, propyl, butyl, pentyl, hexyl, and the like. An appropriate solvent may be selected as the first solvent depending on the first pigment.

To prepare the first pigment dispersion, the first solvent and the first dispersant may be uniformly mixed, and the first pigment may be added thereto for mixing, so as to prepare a first mixture. Alternatively, the first dispersant and the first pigment may be added to the first solvent for mixing, so as to prepare a first mixture. The mixing order of the first pigment, the first dispersant, and the first solvent may be appropriately changed. Regarding the first mixture, for example, the first pigment dispersion may be prepared by dispersion using bead mills, but the dispersion method for the first mixture is not limited to the bead mills.

The second pigment may be a pigment for presenting desired color on the hair whose original color is masked by the first pigment. As the second pigment, various pigments may be used according to desired color. The second pigment may include, for example, prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS(CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof, but embodiments are not limited thereto. The content of the second pigment may be about 10 wt % to about 60 wt % based on the entire second pigment dispersion.

The second dispersant may use, as a material added to the second solvent to prevent aggregation of the second pigment, a surfactant or a polymer. For use as the second dispersant, polyvinyl pyrrolidone, polyvinyl alcohol, polyvinyl acetate, a pyrrolidone/acrylic acid copolymer, a pyrrolidone/methacrylic acid copolymer, a styrene/acrylic acid copolymer, a styrene/methacrylic acid copolymer, a styrene/maleic anhydride copolymer, an acrylic acid alkyl ester/acrylic acid copolymer, a methacrylic acid alkyl ester/acrylic acid copolymer, polyvinyl oxazoline, polyvinyl imidazole, polyethylene glycol, polypropylene glycol, a polyglyceryl-ester-based dispersant, such as polyquaternium-51, polyquaternium-10, glyceryl stearate, polysorbate 20, polysorbate 80, polysorbate 60, lecithin, polyglyceryl-10, and polyglyceryl-6 polyricinoleate, a polyglycerin fatty acid ester-based dispersant, or a combination thereof may be used. Alkyl among the compounds may be, for example, methyl, ethyl, propyl, butyl, pentyl, hexyl, and the like.

In addition, for use as the dispersant, a commercially available dispersant may be used. For example, the dispersant may include DISPERBYK-111, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-161, DISPERBYK-163, DISPERBYK-185, DISPERBYK-2001, DISPERBYK-187, DISPERBYK-190, DISPERBYK-109, DISPERBYK-2163, DISPERBYK-184, DISPERBYK-2155, DISPERBYK-180, DISPERBYK-194 N, TEGO® Dispers 755 W, Efka® PX 4300, Efka® PX 4320, Efka PX 4340, TEGO® Dispers 655, or a combination thereof, but embodiments are not limited thereto.

The content of the second dispersant may be about 5 wt % to about 30 wt % based on the entire second pigment dispersion. When the contents of the second pigment and the second dispersant are within the ranges above, the second pigment dispersion may have excellent dispersibility leading to long-term stability, and have uniform hair color-expressing characteristics.

The second solvent may use, as a solvent for forming the second pigment dispersion, distilled water, diethylene glycol butyl ether, ethylene glycol, propylene glycol, polyethylene glycol, glycerin, oleyl alcohol, butylene glycol dimethylsiloxane, cyclopentasiloxane, ethyl alcohol, n-propyl alcohol, isopropyl alcohol, n-butyl alcohol, sec-butyl alcohol, t-butyl alcohol, isobutyl alcohol, ethyl lactate, diethylene glycol, triethylene glycol, dipropylene glycol, butylene glycol, 1,4-butanediol, 1,2,4-butanetriol, 1,5-pentanediol, 1,6-hexanediol, 1,2-hexanediol, 1,2,6-hexanetriol, hexylene glycol, glycerol ethoxylate, trimethylol propane ethoxylate, sodium 2-pyrrolidone-5-carboxylate, methyl pyrrolidone, caprylyl pyrrolidone, erythritol, ethyleneglycol monomethyl ether, ethyleneglycol monoethyl ether, diethylene glycol methyl ether, diethylene glycol ethyl ether, triethyleneglycol monomethyl ether, triethyleneglycol monoethyl ether, dimethyl sulfoxide, tetramethylene sulfone, thioglycol, methylcarbitol, ethylcarbitol, propylcarbitol, butylcarbitol, alkyl cellosolve, dipropylene glycol alkyl ether, carbitol monoalkyl acetate, propylene glycol monoalkyl ether, ethylene carbonate, propylene carbonate, butanol, pentanol, hexanol, 2-etheylhexanol, or a combination thereof, but embodiments are not limited thereto. Alkyl among the compounds may be, for example, methyl, ethyl, propyl, butyl, pentyl, hexyl, and the like. For use as the second solvent, a material identical to or different from the first solvent may be used. An appropriate solvent may be selected as the second solvent depending on the second pigment.

In the same manner as in the preparation of the first pigment dispersion, the second solvent and the second dispersant may be uniformly mixed, and the second pigment may be added thereto for mixing, so as to prepare a second mixture. Alternatively, the second dispersant and the second pigment may be added to the second solvent for mixing, so as to prepare a second mixture. The mixing order of the second pigment, the second dispersant, and the second solvent may be appropriately changed. Regarding the second mixture, for example, the second pigment dispersion may be prepared by dispersion using bead mills, but the dispersion method for the second mixture is not limited to the bead mills.

Subsequently, the first pigment dispersion and the second pigment dispersion may be mixed to prepare a mixed dispersion (S20). Here, the first pigment dispersion and the second pigment dispersion may be mixed to have a weight ratio of the first pigment to the second pigment in the mixed dispersion in a range of 2:1 to 1:5. When the weight ratio of the first pigment to the second pigment is within the range above, the dyeing of the hair may be efficiently achieved.

An ink composition for hair dyeing may be prepared by adding and mixing a resin, wax, and a third solvent to the mixed dispersion (S30).

The resin disperses the first pigment and the second pigment, and may also provide transfer characteristics by imparting adhesion strength to the ink layer for hair dyeing on a base film and hair. The resin may include a polymer including at least one unit of acrylate, dimethylsiloxane, cyclopentasiloxane, polyacrylic acid, sodium polyacrylate, partially neutralized polyacrylic acid, polyacrylate starch, carmellose sodium, a carboxyvinyl polymer, an N-vinylacetatamide copolymer, polyurethane, polyester urethane, carboxymethyl cellulose, methyl cellulose, ethyl cellulose, hydroxypropyl cellulose, hydroxypropylmethyl cellulose, hydroxyethyl cellulose, polyvinyl pyrrolidone, polyvinyl alcohol, polyvinyl acetoacetal, polyvinyl butyral, polyquaternium-28, polyquaternium-11, an acrylate/dimethylsilicone copolymer, a vinylacetate/vinylpyrrolidonemonomer copolymer, a vinylpyrrolidone/dimethylamino ethylmetaacrylate copolymer, a styrene/acrylate copolymer, an acrylate/ethylhexylacrylate copolymer, dextrinisostearate, a metacryloyl ethylbetaine/acrylate copolymer, an AMP/acrylate copolymer, cellulose acetate formate, cellulose acetate propionate, and cellulose acetate butylate. The resin may be, for example, an acrylate/dimethylsilicone copolymer.

The wax may further impart adhesion strength to the ink layer for hair dyeing on the hair, and may facilitate transfer from a base, such as a film, to the hair when heat is applied. The wax may use, for example, carnauba wax, lanolin, paraffin, shea butter, beeswax, olive wax, candelilla wax, vegetable wax, cacao butter, microcrystal wax, ceresin wax, cupuacu seed butter, braze, caster oil, polyethylene wax, microcrystalline wax, amide wax, ester wax, oxidation wax, or a combination thereof, but embodiments are not limited thereto.

The third solvent may use, as a solvent for viscosity control and uniform mixing properties, methyl ethyl ketone, ethyl acetate, ethyl ether, diethylene glycol butyl ether, ethylene glycol, propylene glycol, polyethylene glycol, dimethyl siloxane, cyclopentasiloxane, ethanol, acetone, diethylene glycol butyl ether, ethylene glycol, propylene glycol, polyethylene glycol, glycerin, oleyl alcohol, butylene glycol dimethyl siloxane, cyclopentasiloxane, ethyl alcohol, n-propyl alcohol, isopropyl alcohol, n-butyl alcohol, sec-butyl alcohol, t-butyl alcohol, isobutyl alcohol, ethyl lactate, diethylene glycol, triethylene glycol, dipropylene glycol, butylene glycol, 1,4-butanediol, 1,2,4-butanetriol, 1,5-pentanediol, 1,6-hexanediol, 1,2-hexanediol, 1,2,6-hexanetriol, hexylene glycol, glycerol ethoxylate, trimethylol propane ethoxylate, sodium 2-pyrrolidone-5-carboxylate, methyl pyrrolidone, caprylyl pyrrolidone, erythritol, ethyleneglycol monomethyl ether, ethyleneglycol monoethyl ether, diethylene glycol methyl ether, diethylene glycol ethyl ether, triethyleneglycol monomethyl ether, triethyleneglycol monoethyl ether, dimethyl sulfoxide, tetramethylene sulfone, thioglycol, methylcarbitol, ethylcarbitol, propylcarbitol, butylcarbitol, alkyl cellosolve, dipropyleneglycol alkylether, carbitol monoalkyl acetate, propylene glycol monoalkyl ether, ethylene carbonate, propylene carbonate, butanol, pentanol, hexanol, 2-ethylhexanol, or a combination thereof, but embodiments are not limited thereto. Alkyl among the compounds may be, for example, methyl, ethyl, propyl, butyl, pentyl, hexyl, and the like.

For use as the third solvent, a material identical to or different from the first solvent or the second solvent may be used.

Subsequently, the ink composition for hair dyeing is applied onto a base film (S40). For use as the base film, a heat-resistant film for supporting and transferring the ink layer for hair dyeing may be used. The base film may use PET, PEN, PE, PI, PC, PP, polyester, or a combination thereof, but embodiments are not limited thereto. The base film 1 may have, for example, a thickness in a range of 2 μm to 20 μm. The ink composition for hair dyeing may be applied to or coated on the base film by, for example, bar coating, micro-gravure printing, gravure printing, slit die printing, flexo printing, and the like.

Subsequently, the base film coated with the ink composition for hair dyeing is dried to complete the preparation of a film for hair dyeing (S50). In the film for hair dyeing, an ink layer for dyeing may have a thickness in a range of 1 μm to 100 μm. When the ink layer for dyeing has the thickness in the range above, the ink layer can efficiently receive heat from the printer head and can be transferred from the base film to the hair efficiently, upon the operation of the printer for hair dyeing.

The hair dyeing according to embodiments is printing-type dry dyeing. Thus, since the hair does not undergo a process of applying a hair dyeing paste to the hair and shampooing and rinsing, it is easy and quick to temporarily dye the hair, and the dye does not come out. In addition, the dye of the hair dyed according to embodiments can be easily removed by shampoo or the like.

Hereinabove, the preferable embodiments of the present disclosure have been described with reference to drawings and Examples, but these are only exemplary, and those skilled in the art can understand that various modifications and equivalent other embodiments are possible therefrom. Therefore, the scope of protection of the present disclosure should be defined by the appended claims.

MODE FOR INVENTION

Hereinafter, the present disclosure will be described in detail with reference to the following examples, but the present disclosure is not limited to the following examples.
(Preparation of Ink Composition for Hair Dyeing)

Example 1

8.0 g of a titanium oxide pigment ($TiO_2$, by Sunchemical Company), 3.0 g of polyvinyl pyrrolidone, 10.0 g of diethylene glycol butyl ether, 8.0 g of diethylene glycol, and 2.0 g of trimethylolpropane were put together and mixed using bead mills for 2 hours to prepare a uniform dispersion. The dispersion was filtered through a 0.45 micron (μm) filter to prepare a first pigment dispersion.

8.0 g of a blue pigment (pigment blue 15 (CI74160), by Clarient Company), 1.0 g of polysorbate-20, 12.0 g of water, 5.0 g of diethylene glycol, 5.0 g of trimethylolpropane, and 8.0 g of glycerin were put together and sufficiently mixed using a homogenizer for at least 30 minutes to prepare a uniform dispersion. The dispersion was filtered through a 0.45 μm filter to prepare a second pigment dispersion.

The prepared first and second pigment dispersions were mixed for at least 30 minutes. 6.0 g of an acrylate resin, 3.0 g of carnauba wax, 5.0 g of lanolin wax, and 16.0 g of methylethyl ketone were added to the mixed dispersion, and the mixed solution was stirred in a sealed container while heating at 70° C. to prepare a uniform ink composition for hair dyeing.

Example 2

An ink composition for hair dyeing was prepared in the same manner as in Example 1, except that, in preparing the first pigment dispersion, an aluminum oxide pigment was used instead of the titanium oxide pigment.

Example 3

12.0 g of a titanium oxide pigment ($TiO_2$, by Sunchemical Company), 2.0 g of polyquaternium-51, 15.0 g of ethylene glycol, and 15.0 g of isobutyl alcohol were put together and mixed using bead mills for 3 hours to prepare a uniform dispersion. The dispersion was filtered through a 0.45 μm filter to prepare a first pigment dispersion.

6.0 g of a red pigment (pigment red 5 (CI12490), by Clarient Company), 4.0 g of polyvinyl alcohol, 4.0 g of 1,2-hexanediol, 4.0 g of pentanol, and 4.0 g of glycerin were put together and mixed using a homogenizer for at least 1 hour to prepare a uniform dispersion. The dispersion was filtered through a 0.45 μm filter to prepare a second pigment dispersion.

The prepared first and second pigment dispersions were mixed for at least 30 minutes. 5.0 g of a polyurethane resin, 3.0 g of polyvinyl butyral, 10.0 g of shea butter wax, 6.0 g of candelilla wax, and 10.0 g of cyclopentasiloxane were added to the mixed dispersion, and the mixed solution was stirred in a sealed container while heating at 80° C. to prepare a uniform ink composition for hair dyeing.

Example 4

An ink composition for hair dyeing was prepared in the same manner as in Example 3, except that, in preparing the first pigment dispersion, an aluminum oxide pigment was used instead of the titanium oxide pigment.

Example 5

3.0 g of a titanium oxide pigment ($TiO_2$, by Sunchemical Company), 0.5 g of polyvinyl acetate, 2.0 g of trimethylol propane, and 3.0 g of diethylene glycol were put together and mixed using bead mills for 1 hour to prepare a uniform dispersion. The dispersion was filtered through a 0.45 μm filter to prepare a first pigment dispersion.

13.0 g of a yellow pigment (pigment yellow 1 (CI11680), by Clarient Company), 5.0 g of polyvinyl acetate, 2.5 g of DISPERBYK-111, 8.0 g of ethyl lactate, and 12.0 g of thioglycol were put together and mixed using bead mills for 3 hours to prepare a uniform dispersion. The dispersion was filtered through a 0.45 μm filter to prepare a second pigment dispersion.

The prepared first and second pigment dispersions were mixed for at least 30 minutes. 5.0 g of a polyurethane resin, 5.0 g of a polyester urethane resin, 5.0 g of paraffin, 8.0 g of beeswax, 13 g of carnauba wax, 10 g of n-propyl alcohol, and 5 g of n-butyl alcohol were added to the mixed dispersion, and the mixed solution was stirred in a sealed container while heating at 80° C. to prepare a uniform ink composition.

Example 6

An ink composition for hair dyeing was prepared in the same manner as in Example 5, except that, in preparing the first pigment dispersion, an aluminum oxide pigment was used instead of the titanium oxide pigment.

Comparative Example 1

16.0 g of a blue dye (D&C Blue No. 9, by Kishi Kasei Company), 24.0 g of ethyl alcohol, and 30 g of diethylene glycol were put together and sufficiently mixed using a homogenizer for at least 30 minutes to prepare a uniform dispersion. 6 g of an acrylate resin, 3.0 g of carnauba wax, 5.0 g of lanolin wax, and 16 g of methyl ethyl ketone were added to the dispersion, and the mixed solution was stirred in a sealed container while heating at 70° C. to prepare a uniform ink composition for hair dyeing.

Comparative Example 2

8.0 g of a titanium oxide pigment ($TiO_2$, by Sunchemical Company), 8.0 g of a blue dye (D&C Blue No. 9, by Kishi Kasei Company), 4.0 g of polyvinyl pyrrolidone, 20.0 g of ethyl alcohol, and 30.0 g of diethylene glycol were put together and mixed using bead mills for 3 hours to prepare a uniform dispersion. The dispersion was filtered through a 0.45 μm filter. 6 g of an acrylate resin, 3.0 g of carnauba wax, 5.0 g of lanolin wax, and 16 g of methylethyl ketone were added to the filtrate, and the mixed solution was stirred in a sealed container while heating at 70° C. to prepare a uniform ink composition for hair dyeing.

Comparative Example 3

18.0 g of a red dye (FD&C Red No. 4, by Kishi Kasei Company), 30.0 g of distilled water, and 18.0 g of glycerin were put together and sufficiently mixed using a homogenizer for at least 30 minutes to prepare a uniform dispersion. 5.0 g of a polyurethane resin, 3.0 g of polyvinyl butyral, 10.0 g of shea butter wax, 6.0 g of candelilla wax, and 10.0 g of cyclopentasiloxane were added to the dispersion, and the mixed solution was mixed in a sealed container while heating at 80° C. to prepare a uniform ink composition for hair dyeing.

Comparative Example 4

12.0 g of an aluminum oxide pigment, 6.0 g of a red dye (FD&C Red No. 4, by Kishi Kasei Company), 2.0 g of polyquaternium-51, and 30.0 g of distilled water, and 16.0 g of glycerin were put together and mixed using bead mills for 2 hours to prepare a uniform dispersion. The dispersion was filtered through a 0.45 μm filter. 5.0 g of a polyurethane resin, 3.0 g of polyvinyl butyral, 10.0 g of shea butter wax, 6.0 g of candelilla wax, and 10.0 g of cyclopentasiloxane were added to the filtrate, and the mixed solution was mixed in a sealed container while heating at 80° C. to prepare a uniform ink composition for hair dyeing.

Comparative Example 5

16.0 g of a yellow dye (FD&C Yellow No. 6, by Flavorchem Company), 13.0 g of ethylene glycol, and 23.0 g of 1,2-hexane diol were put together and sufficiently mixed using a homogenizer for at least 30 minutes to prepare a uniform dispersion. 5.0 g of polyurethane, 5.0 g of polyester urethane, 5.0 g of paraffin wax, 8.0 g of beeswax, 10.0 g of carnauba wax, 10 g of n-propyl alcohol, and 5.0 g of n-butyl alcohol were added to the dispersion, and the mixed solution was mixed in a sealed container while heating at 80° C. to prepare a uniform ink composition for hair dyeing.

Comparative Example 6

3.0 g of a titanium oxide pigment ($TiO_2$, by Sunchemical Company), 13.0 g of a yellow dye (FD&C Yellow No. 6, by Flavorchem Company), 8.0 g of polyvinyl acetate, 13.0 g of ethylene glycol, and 15.0 g of 1,2-hexanediol were put together and mixed using bead mills for 3 hours to prepare a uniform dispersion. The dispersion was filtered through a 0.45 μm filter. 5.0 g of polyurethane, 5.0 g of polyester urethane, 5.0 g of paraffin wax, 8.0 g of beeswax, 10.0 g of carnauba wax, 10 g of n-propyl alcohol, and 5.0 g of n-butyl alcohol were added to the dispersion, and the mixed solution was mixed in a sealed container while heating at 80° C. to prepare a uniform ink composition for hair dyeing. Conditions for preparing the ink compositions for hair dyeing of Examples 1 to 6 and Comparative Examples 1 to 6 are shown in Table 1.

TABLE 1

|  | Example 1 | Example 2 | Example 3 | Example 4 | Example 5 | Example 6 |
|---|---|---|---|---|---|---|
| Pigment for masking | TiO$_2$ | Al$_2$O$_3$ | TiO$_2$ | Al$_2$O$_3$ | TiO$_2$ | Al$_2$O$_3$ |
| First dispersant | Polyvinyl pyrrolidone | | Polyquaternium-51 | | Polyvinyl acetate | |
| First solvent | Diethylene glycol butyl ether, diethylene glycol, and trimethylol propane | | Ethylene glycol and isobutyl alcohol | | Trimethylol propane and diethylene glycol | |
| Pigment for expression | Blue (Pigment blue 15 (CI74160)) | | Red (Pigment red 5 (CI12490)) | | Yellow (Pigment yellow 1 (CI11680)) | |
| Second dispersant | Polysorbate-20 | | Polyvinyl alcohol | | DISPERBYK-111 Polyvinyl acetate | |
| Second solvent | Water, diethylene glycol, trimethylol propane, and glycerin | | 1,2-hexanediol, pentanol, and glycerin | | ethyl lactate and thioglycol | |
| Resin | Acrylate resin | | Polyurethane resin and polyvinyl butyral resin | | Polyurethane resin and polyester urethane resin | |
| Wax | Carnauba wax and lanolin wax | | Shea butter wax and candelilla wax | | paraffin, beeswax, and carnauba wax | |
| Third solvent | Methylethyl ketone | | Cyclopentasiloxane | | n-propyl alcohol and n-butyl alcohol | |
| Dispersion process | Pigment for masking and pigment for expression are separately dispersed | | | | | |

|  | Comparative Example 1 | Comparative Example 2 | Comparative Example 3 | Comparative Example 4 | Comparative Example 5 | Comparative Example 6 |
|---|---|---|---|---|---|---|
| Pigment for masking | Not used | TiO$_2$ | Not used | Al$_2$O$_3$ | Not used | TiO$_2$ |
| First dispersant | Not used | Polyvinyl pyrrolidone | Not used | Polyquaternium-51 | Not used | Polyvinyl acetate |
| Pigment for expression | Blue (D&C Blue No. 9) | | Red (FD&C Red No. 4) | | Yellow (FD&C Yellow No. 6) | |
| First solvent | Ethyl alcohol and diethylene glycol | | Distilled water and glycerin | | Ethylene glycol and 1,2-hexanediol | |
| Resin | Acrylate resin | | Polyurethane resin and polyvinyl butyral resin | | Polyurethane resin and polyester urethane resin | |
| Wax | Carnauba wax and lanolin wax | | Shea butter wax and candelilla wax | | paraffin, beeswax, and carnauba wax | |
| Second solvent | Methylethyl ketone | | Cyclopentasiloxane | | n-propyl alcohol and n-butyl alcohol | |
| Dispersion process | Pigment for masking and pigment for expression are dispersed together | | | | | |

(Preparation of Film for Hair Dyeing)

Each of the ink compositions for hair dyeing of Examples 1 to 6 and Comparative Examples 1 to 6 was coated on a PET base film to a thickness of 35 μm, primarily dried at 70° C., and then secondarily dried at 130° C. to prepare a film for hair dyeing.

(Hair Printing)

Examples 7 to 12 and Comparative Examples 7 to 12

The printer for hair dyeing (Prinker Hair, by Prinker Korea Company)(as a thermal transfer head, KPZ-72-8PBQ1-STA by KYOCERA included) according to an embodiment of the present disclosure and the film for hair dyeing prepared by using each of the ink compositions for hair dyeing of Examples 1 to 6 and Comparative Examples 1 to 6 were used for hair printing of Examples 7 to 12 and Comparative Examples 7 to 12 by printing and dyeing bar-shaped patterns (1 cm×2 cm) on black human hair. That is, human hair covered with the film for hair dyeing was placed between the body and the hair holder of the printer for hair dyeing, and the printer for hair dyeing was held so that the body and the hair holder can press down the film for hair dyeing and the human hair. Then, the printer for hair dyeing is operated by moving it over the human hair in the longitudinal direction to dye the human hair by a hair printing method. Here, the head of the printer for hair dyeing was heated up to 200° C.

Evaluation of Hair Color Development

Optical density (OD) of the dyed human hair was measured by using a spectroeye (by GretagMacbeth Company) which is a colorimetric densitometer, and then evaluated according to the following criteria. The evaluation results are shown in Table 2. The OD refers to a logarithmic value of a ratio ($I_0/I_1$) of the amount of illuminated radiation ($I_0$) to the amount of transmitted radiation ($I_1$), when energy of light or the like is applied to a material.

When the OD is measured, color sharpness which includes both brightness and chroma in a corresponding color can be measured as an objective indicator, and thus OD can be used as a criterion for evaluating color development when dyeing hair.

Good (○): OD>0.7

Moderate (Δ): 0.5≤OD<0.7

Poor (x): OD<0.5

TABLE 2

|  | Example 7 | Example 8 | Example 9 | Example 10 | Example 11 | Example 12 |
|---|---|---|---|---|---|---|
| OD value | 0.86 | 0.77 | 0.90 | 0.82 | 0.76 | 0.71 |
| evaluation | ○ | ○ | ○ | ○ | ○ | ○ |

|  | Comparative Example 7 | Comparative Example 8 | Comparative Example 9 | Comparative Example 10 | Comparative Example 11 | Comparative Example 12 |
|---|---|---|---|---|---|---|
| OD value | 0.45 | 0.67 | 0.47 | 0.68 | 0.42 | 0.65 |
| evaluation | x | Δ | x | Δ | x | Δ |

Referring to Table 2, in Examples 7 to 12, all OD values were 0.7 or more, indicating that the hair color development was excellent and a desired color was realized. However, in Comparative Examples 7 to 12, OD values were less than 0.7, indicating that the color development was insufficient.

Evaluation of Water Resistance

In Examples 7 to 12 and Comparative Examples 7 to 12, after the printed part of the hair was immersed in water for 5 minutes, removed, and then completely dried, OD ($OD_{wet}$) was measured. A percentage of OD ($OD_{wet}$) to OD ($OD_{before}$) measured before the immersion in water was obtained and evaluated according to the following criteria, and the results are shown in Table 3.

$$A = (OD_{wet}/OD_{before}) \times 100 (\%)$$

Good (○): A>90
Moderate (Δ): 70≤A<90
Poor (x): A<70

TABLE 3

|  | Example 7 | Example 8 | Example 9 | Example 10 | Example 11 | Example 12 |
|---|---|---|---|---|---|---|
| $OD_{before}$ | 0.86 | 0.77 | 0.90 | 0.82 | 0.76 | 0.71 |
| $OD_{wet}$ | 0.82 | 0.71 | 0.84 | 0.77 | 0.71 | 0.65 |
| A value | 95 | 92 | 93 | 94 | 93 | 91 |
| Evaluation | ○ | ○ | ○ | ○ | ○ | ○ |

|  | Comparative Example 7 | Comparative Example 8 | Comparative Example 9 | Comparative Example 10 | Comparative Example 11 | Comparative Example 12 |
|---|---|---|---|---|---|---|
| $OD_{before}$ | 0.45 | 0.67 | 0.47 | 0.68 | 0.42 | 0.65 |
| $OD_{wet}$ | 0.18 | 0.25 | 0.19 | 0.23 | 0.16 | 0.28 |
| A value | 40 | 37 | 40 | 34 | 38 | 43 |
| evaluation | x | x | x | x | x | x |

Referring to Table 3, it was confirmed that Examples 7 to 12 had excellent water resistance due to a small difference in the hair color development before and after the immersion in water compared to Comparative Examples 7 to 12.

Evaluation of Abrasion Resistance

In Examples 7 to 12 and Comparative Examples 7 to 12, after 5 minutes of hair dyeing, the dyed part of the hair was rubbed 5 times using a tester, and GD ($OD_{abbr}$) was measured and a percentage of GD ($OD_{abbr}$) to GD ($OD_{before}$) measured before the rubbing was obtained and evaluated according to the following criteria, and the results are shown in Table 4.

$$B = (OD_{abbr}/OD_{before}) \times 100 (\%)$$

Good (○): B>90
Moderate (Δ): 70≤B<90
Poor (x): B<70

TABLE 4

|  | Example 7 | Example 8 | Example 9 | Example 10 | Example 11 | Example 12 |
|---|---|---|---|---|---|---|
| $OD_{before}$ | 0.86 | 0.77 | 0.90 | 0.82 | 0.76 | 0.71 |
| $OD_{abbr}$ | 10.78 | 0.70 | 0.83 | 0.75 | 0.70 | 0.66 |
| B value | 91 | 91 | 92 | 91 | 92 | 93 |
| evaluation | ○ | ○ | ○ | ○ | ○ | ○ |

TABLE 4-continued

|  | Comparative Example 7 | Comparative Example 8 | Comparative Example 9 | Comparative Example 10 | Comparative Example 11 | Comparative Example 12 |
|---|---|---|---|---|---|---|
| $OD_{before}$ | 0.45 | 0.67 | 0.47 | 0.68 | 0.42 | 0.65 |
| $OD_{abbr}$ | 0.38 | 0.42 | 0.35 | 0.41 | 0.35 | 0.39 |
| B value | 84 | 67 | 74 | 60 | 83 | 60 |
| evaluation | Δ | x | Δ | x | Δ | x |

Referring to Table 4, it was confirmed that Examples 7 to 12 had excellent wear resistance from a small difference in the hair color development before and after the rubbing compared to Comparative Examples 7 to 12.

Evaluation of Dyeing Removal 1 day after the hair dyeing according to Examples 7 to 12 and Comparative Examples 7 to 12, the dyed hair was rubbed in water with shampoo for 5 minutes, completely dried, and then OD ($OD_{shampoo}$) was measured. Then, a percentage of OD ($OD_{shampoo}$) to OD ($OD_{before}$) measured before the shampooing was obtained and evaluated according to the following criteria, and the results are shown in Table 5.

$C = (OD_{shampoo}/OD_{before}) \times 100(\%)$

Good (○): C<10
Moderate (Δ): 10≤C<30
Poor (x): C>30

TABLE 5

|  | Example 7 | Example 8 | Example 9 | Example 10 | Example 11 | Example 12 |
|---|---|---|---|---|---|---|
| $OD_{before}$ | 0.86 | 0.77 | 0.90 | 0.82 | 0.76 | 0.71 |
| $OD_{shampoo}$ | 0.08 | 0.07 | 0.08 | 0.07 | 0.07 | 0.06 |
| C value | 9 | 9 | 9 | 8 | 9 | 8 |
| evaluation | ○ | ○ | ○ | ○ | ○ | ○ |

|  | Comparative Example 7 | Comparative Example 8 | Comparative Example 9 | Comparative Example 10 | Example 11 Comparative | Example 12 Comparative |
|---|---|---|---|---|---|---|
| $OD_{before}$ | 0.45 | 0.67 | 0.47 | 0.68 | 0.42 | 0.65 |
| $OD_{shampoo}$ | 0.15 | 0.15 | 0.18 | 0.17 | 0.13 | 0.17 |
| C value | 33 | 22 | 38 | 25 | 31 | 26 |
| evaluation | × | Δ | × | Δ | × | Δ |

Referring to Table 5, it was confirmed that Examples 7 to 12 showed a significant difference in the hair color development after the shampooing compared to Comparative Examples 7 to 12, indicating that the dye was well removed.

The invention claimed is:

1. An ink composition for hair dyeing comprising:
   a first pigment dispersion comprising a first pigment, a first dispersant and a first solvent for masking hair color;
   a second pigment dispersion comprising a second pigment, a second dispersant and a second solvent for expressing desired color on hair;
   a resin;
   wax; and
   a solvent,
   wherein the first dispersant and the second dispersant are different each other.

2. The ink composition of claim 1, wherein the first pigment comprises titanium oxide, tin oxide, zinc oxide, aluminum oxide, silicon dioxide, zirconium oxide, silver (I) oxide, gold, silver, mica, synthetic mica, or a combination thereof.

3. The ink composition of claim 1, wherein the second pigment comprises prussian blue (CI77510), pigment red 5 (CI12490), pigment red 63:1 (CI15880), pigment red 57:1 (CI15850), pigment red 181 (CI73360), ultramarine pink (CI77077), carmine (CI75470), red iron oxide (CI77491), blue 1 (CI42090), pigment blue 15 (CI74160), ultramarine (CI77007), pigment yellow 1 (CI11680), tartrazine (CI19140), quinoline yellow WS (CI47005), sunset yellow (CI15985), yellow iron oxide (CI77492), chromium oxide green (CI77288), chromium hydroxide green (CI77289), manganese violet (CI77742), ultramarine violet (CI77077), black iron oxide (CI77499), carbon black (CI77266), fluorescent pigment, phosphorescent pigment, luminescent zinc sulfide, or a combination thereof.

4. A film for hair dyeing comprising:
   a base film; and
   an ink layer for hair dyeing on the base film,
   wherein the ink layer for hair dyeing is formed by the ink composition for hair dyeing according to claim 1.

5. The film of claim 4, further comprising a back film on a counter side facing the ink layer on the base film.

6. A film cartridge for hair dyeing comprising:
   a pair of reels comprising a first reel and a second reel;
   the film for hair dyeing according to claim 4 wound around the first reel and having one end connected to the second reel; and
   a cartridge housing protecting the first reel, the second reel, and the film and comprising a film-exposing unit positioned between the first reel and the second reel and exposing the film for hair dyeing.

7. A printer for hair dyeing comprising:
   a body comprising a printer head; and
   a hair holder of which one end is connected to one end of the body so as to be folded and unfolded with respect to the body,
   wherein the hair is grabbed between the body and the hair holder,
   the printer head is positioned on a side facing the hair holder, and
   the film for hair dyeing is positioned between the body and the hair, wherein the film for hair dyeing comprises:

a base film; and an ink layer for hair dyeing on the base film, and wherein the ink layer for hair dyeing is formed by the ink composition for hair dyeing according to claim 1.

8. The printer of claim 7, wherein the printer head is in contact with the film for hair dyeing.

9. The printer of claim 7, wherein the printer head is a thermal transfer type.

10. The printer of claim 7, wherein heat is applied to each dot of the printer head independently, so as to form a dyeing pattern on the hair.

11. The printer of claim 7, wherein the hair holder is a roller type.

12. The printer of claim 7, wherein the body comprises an operating unit and display unit.

13. A printer for hair dyeing comprising:

a body comprising a printer head; and a hair holder of which one end is connected to one end of the body so as to be folded and unfolded with respect to the body, wherein the hair is grabbed between the body and the hair holder, the printer head is positioned on a side facing the hair holder, wherein the body further comprises a cartridge mounting unit to which a film cartridge for hair dyeing according to claim 6 is mounted so as to connect the body with the printer head.

\* \* \* \* \*